United States Patent
Hatakeyama et al.

(10) Patent No.: US 7,402,712 B2
(45) Date of Patent: Jul. 22, 2008

(54) ADAMANTYL VINYL ETHER COMPOUND AND PRODUCTION PROCESS FOR THE SAME

(75) Inventors: Naoyoshi Hatakeyama, Yamaguchi (JP); Shinji Tanaka, Yamaguchi (JP); Hidetoshi Ono, Yamaguchi (JP); Kouichi Kodoi, Yamaguchi (JP)

(73) Assignee: Idemitsu Petrochemical Co., Ltd., Tokyo (JP)

( * ) Notice: Subject to any disclaimer, the term of this patent is extended or adjusted under 35 U.S.C. 154(b) by 85 days.

(21) Appl. No.: 10/862,423

(22) Filed: Jun. 8, 2004

(65) Prior Publication Data
US 2005/0004391 A1    Jan. 6, 2005

(30) Foreign Application Priority Data
Jun. 9, 2003    (JP) .............................. 2003-163320

(51) Int. Cl.
*C07C 43/18*    (2006.01)

(52) U.S. Cl. .................... 568/665; 568/361; 568/372; 568/375; 568/612; 568/669; 568/670; 560/116; 562/498

(58) Field of Classification Search .................. 568/669
See application file for complete search history.

(56) References Cited

U.S. PATENT DOCUMENTS

| 2003/0194643 | A1 |  | 10/2003 | Choi | ....................... 430/270.1 |
| 2005/0288528 | A1 | * | 12/2005 | Okazoe et al. | .............. 562/849 |

FOREIGN PATENT DOCUMENTS

| EP | 1 288 186 A2 | 3/2003 |
| JP | 2000-089463 | * 3/2000 |

OTHER PUBLICATIONS

Patent Abstracts of Japan, JP 2003-212823, Jul. 30, 2003.
Yoshio Okimoto, et al., "Development of a Highly Efficient Catalytic Method for Synthesis of Vinyl Ethers", Journal of the American Chemical Society, XP-002297062, vol. 124, No. 8, 2002, pp. 1590-1591.

* cited by examiner

*Primary Examiner*—Rosalynd Keys
(74) *Attorney, Agent, or Firm*—Oblon, Spivak, McClelland, Maier & Neustadt, P.C.

(57) ABSTRACT

Provided by the present invention are an adamantyl vinyl ether compound which is useful as a monomer for functional resins in the photolithography field or a raw material therefor and medical and agricultural intermediates and a production process for the same.

The present invention relates to a production process for an adamantyl vinyl ether compound, characterized by subjecting an adamantyl vinyl ether compound having a specific structure and alcohol having an eliminating group in a β position to chloroalkyl-etherification, then subjecting it to etherification to form an adamantyl group-containing ether and then subjecting it to vinyl-etherification.

4 Claims, No Drawings

ADAMANTYL VINYL ETHER COMPOUND AND PRODUCTION PROCESS FOR THE SAME

TECHNICAL FIELD

The present invention relates to a novel adamantyl vinyl ether compound and a production process for the same, more specifically to a novel adamantyl vinyl ether compound which is useful as a monomer for functional resins (a photosensitive resin and the like) in the photolithography field or a raw material therefor, a resin additive (a heat resistance-improving agent and the like), other various additives (an acidity-raising agent, a fat solubility-raising agent and the like), medical and agricultural intermediates and other various industrial products and a production process for efficiently producing the above compound.

RELATED ART

Adamantane has a structure in which four cyclohexane rings are condensed in a cage form and is a stable compound having a high symmetric property, and it has a low dielectric constant which is inherent to an alicyclic compound. It is known that since the derivatives thereof show a specific function, they are useful as, for example, medical raw materials and raw materials for high functional industrial materials. For example, adamantyl acrylate can be used as a resin monomer (for example, Japanese Patent Publication No. 307844/1988) and is highly valued particularly as a photoresist (for example, Japanese Patent No. 2881969). Also, a lactone-containing polymer is used as the other photoresist (for example, Japanese Patent Application Laid-Open No. 82441/2002). Further, they have an optical characteristic and a heat resistance and therefore are tried to be used for an optical disc substrate, an optical fiber and a lens (for example, Japanese Patent Application Laid-Open No. 305044/1994 and Japanese Patent Application Laid-Open No. 302077/1997). Also, it is tried to use adamantane esters as a resin raw material for a photoresist making use of an acid sensitivity, a dry etching resistance and a UV transmission (for example, Japanese Patent Application Laid-Open No. 39665/1992).

Carbon-carbon double bonds are present in polymers obtained from conventional monomers having an ester bond, and this bond does not show absorption in an ArF eximer laser wavelength area (193 nm). However, it shows strong absorption in 157 nm which is an emission wavelength of an $F_2$ eximer laser, and therefore it can not be used as a resist resin cured by the above laser.

The present invention has been made under such circumstances, and an object thereof is to provide a novel adamantyl vinyl ether compound which is useful as a monomer for functional resins (photosensitive resins and the like) in the photolithography field or a raw material therefor, a resin additive (a heat resistance-improving agent and the like), other various additives (an acidity-raising agent, a fat solubility-raising agent and the like), medical and agricultural intermediates and other various industrial products and a production process for efficiently producing the above compound.

DISCLOSURE OF THE INVENTION

Intensive researches repeated by the present inventors in order to develop a novel compound useful for the uses described above have resulted in finding that an adamantyl vinyl ether compound having a specific structure can meet the above object.

The present invention has completed based on such knowledge.

That is, the present invention provides the following novel adamantyl vinyl ether compound and a production process for the same.

(1) An adamantyl vinyl ether compound represented by formula (I):

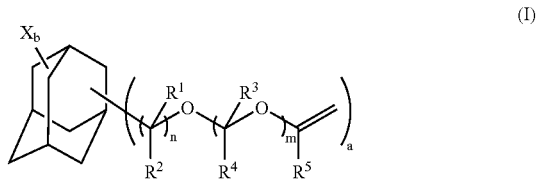

wherein X's each represent independently a hydrogen atom, a halogen atom, an alkyl group having 1 to 10 carbon atoms which may contain a hetero element, a hydroxyl group, an alkoxy group having 1 to 8 carbon atoms, a carboxyl group, COOR (R represents an alkyl group having 1 to 8 carbon atoms) or =O (keto group) formed by putting two X's together; $R^1$, $R^2$, $R^3$ and $R^4$ each represent independently a hydrogen atom, a halogen atom or an alkyl group having 1 to 10 carbon atoms which may contain a hetero element; $R^5$'s each represent independently a hydrogen atom, a halogen atom or an alkyl group having 1 to 3 carbon atoms which may contain a hetero element; m and n each represent an integer of 0 to 10; a represents an integer of 1 to 4; b represents an integer of 12 to 15, and a+b is 16; provided that excluded are a structure in which only 1 to 3 vinyloxy groups are bonded to a bridge head position of the adamantyl group, a structure in which only one vinyloxymethyl group, vinyloxyethyl group or vinyloxypropyl group is bonded to a bridge head position of the adamantyl group and a structure in which only a vinyloxy group and a hydroxyl group are bonded to a bridge head position of the adamantyl group.

(2) The adamantyl vinyl ether compound as described in the above item (1), wherein m is an integer of 1 to 10.

(3) The adamantyl vinyl ether compound as described in the above item (1), having a (vinyloxy)methoxy group.

(4) A production process for the adamantyl vinyl ether compound represented by Formula (I) described above, characterized by subjecting alcohol having an eliminating group in a β position to (a) chloroalkyl-etherification by reacting with hydrogen chloride, then subjecting it to (b) etherification by reacting with an adamantyl group-containing alcohol and a base to form an adamantyl group-containing ether and then subjecting it to (c) vinyl-etherification by reacting with a base.

(5) A production process for the adamantyl vinyl ether compound represented by Formula (I) described above, characterized by subjecting an adamantyl group-containing alcohol to (a) chloroalkyl-etherification by reacting with hydrogen chloride, then subjecting it to (b) etherification by reacting with alcohol having an eliminating group in a β position and a base to form an adamantyl group-containing ether and then subjecting it to (c) vinyl-etherification by reacting with a base.

(6) An adamantyl vinyl ether compound represented by Formula (II):

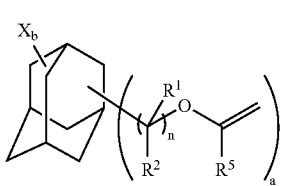

(II)

wherein X's each represent independently a hydrogen atom, a halogen atom, an alkyl group having 1 to 10 carbon atoms which may contain a hetero element, a hydroxyl group, an alkoxy group having 1 to 8 carbon atoms, a carboxyl group, COOR (R represents an alkyl group having 1 to 8 carbon atoms) or =O (keto group) formed by putting two X's together; $R^1$ and $R^2$ each represent independently a hydrogen atom, a halogen atom or an alkyl group having 1 to 10 carbon atoms which may contain a hetero element; $R^5$'s each represent independently a hydrogen atom, a halogen atom or an alkyl group having 1 to 3 carbon atoms which may contain a hetero element; n represents an integer of 0 to 10; a represents an integer of 1 to 4; b represents an integer of 12 to 15, and a+b is 16; provided that excluded are a structure in which only 1 to 3 vinyloxy groups are bonded to a bridge head position of the adamantyl group, a structure in which only one vinyloxymethyl group, vinyloxyethyl group or vinyloxypropyl group is bonded to a bridge head position of the adamantyl group and a structure in which only a vinyloxy group and a hydroxyl group are bonded to a bridge head position of the adamantyl group.

(7) The adamantyl vinyl ether compound as described in the above item (6), having a vinyloxy group.

(8) A production process for the adamantyl vinyl ether compound as described in the above item (6), characterized by reacting an adamantyl group-containing alcohol with an olefin represented by Formula (III) and a base:

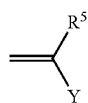

(III)

wherein Y represents an eliminating group; and $R^5$'s each represent independently a hydrogen atom, a halogen atom or an alkyl group having 1 to 3 carbon atoms which may contain a hetero element.

(9) A production process for the adamantyl vinyl ether compound as described in the above item (6), characterized by reacting an adamantyl group-containing alcohol with an acetylene derivative represented by Formula (IV) and a base:

—$R^5$ (IV)

wherein $R^5$'s each represent independently a hydrogen atom, a halogen atom or an alkyl group having 1 to 3 carbon atoms which may contain a hetero element.

EMBODIMENT OF THE INVENTION

The adamantyl vinyl ether compound of the first present invention is a novel compound which is not described in documents and is the adamantyl vinyl ether compound represented by Formula (I):

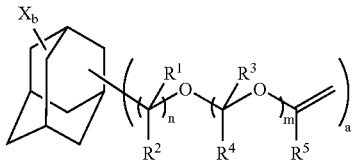

(I)

In Formula (I) described above, the alkyl group having 1 to 10 carbon atoms represented by X, $R^1$, $R^2$, $R^3$ and $R^4$ includes, to be specific, methyl, ethyl, n-propyl, i-propyl, n-butyl, i-butyl, sec-butyl, tert-butyl, n-amyl, i-amyl, n-hexyl, i-hexyl, n-heptyl, i-heptyl, n-octyl, i-octyl, 2-ethyl-hexyl, n-nonyl, i-nonyl, n-decyl and i-decyl.

The halogen atom represented by X, $R^1$, $R^2$, $R^3$ and $R^4$ includes, to be specific, a fluorine atom, a chlorine atom, a bromine atom and an iodine atom.

The alkoxy group having 1 to 8 carbon atoms represented by X includes, to be specific, methoxy, ethoxy, n-propoxy, i-propoxy, n-butoxy, i-butoxybutyl, sec-butoxy, tert-butoxy, n-pentoxy, i-pentoxy, n-hexoxy, i-hexoxy, n-heptoxy, i-heptoxy, n-ocotoxy, i-ocotoxy and 2-ethyl-hexoxy.

COOR (R represents an alkyl group having 1 to 8 carbon atoms) represented by X includes, to be specific, $COOCH_3$, $COOC_2H_5$, $COO\text{-}n\text{-}C_3H_7$, $COO\text{-}i\text{-}C_3H_7$, $COO\text{-}n\text{-}C_4H_9$, $COO\text{-}i\text{-}C_4H_9$, $COO\text{-}sec\text{-}C_4H_9$, $COO\text{-}tert\text{-}C_4H_9$, $COO\text{-}n\text{-}C_5H_{11}$, $COO\text{-}i\text{-}C_5H_{11}$, $COO\text{-}n\text{-}C_6H_{13}$, $COO\text{-}i\text{-}C_6H_{13}$, $COO\text{-}n\text{-}C_7H_{15}$, $COO\text{-}i\text{-}C_7H_{15}$, $COO\text{-}n\text{-}C_8H_{17}$ and $COO\text{-}i\text{-}C_8H_{17}$.

X represents a hydrogen atom, a halogen atom, an alkyl group having 1 to 10 carbon atoms which may contain a hetero element, a hydroxyl group, an alkoxy group having 1 to 8 carbon atoms, a carboxyl group, COOR (R represents an alkyl group having 1 to 8 carbon atoms) or =O (keto group) formed by putting two X's together. They are independent from each other, and all of them may be the same or different.

$R^1$, $R^2$, $R^3$ and $R^4$ represent a hydrogen atom, a halogen atom or an alkyl group having 1 to 10 carbon atoms which may contain a hetero element, and $R^5$ represents a hydrogen atom, a halogen atom or an alkyl group having 1 to 3 carbon atoms which may contain a hetero element. They are independent from each other, and all of them may be the same or different.

The alkyl groups in the alkyl group having 1 to 10 carbon atoms, the alkoxy group having 1 to 8 carbon atoms and the alkoxycarbonyl group in which an alkyl group has 1 to 8 carbon atoms were explained above. They are independent from each other, and all of them may be the same or different.

In Formula (I), m and n each represent an integer of 0 to 10; a represents an integer of 1 to 4; b represents an integer of 12 to 15, and a+b is 16. When they are plural, they may be the same as or different from each other. In Formula (I), however, excluded from the adamantyl vinyl ether compound of the present invention are a structure in which only 1 to 3 vinyloxy groups are bonded to a bridge head position of the adamantyl group, a structure in which only one vinyloxymethyl group, vinyloxyethyl group or vinyloxypropyl group is bonded to a bridge head position of the adamantyl group and a structure in which only a vinyloxy group and a hydroxyl group are bonded to a bridge head position of the adamantyl group.

Among them, the compound having a (vinyloxy)methoxy group is preferred.

The specific examples of the adamantyl vinyl ether compound of the present invention represented by Formula (I) include 1-[(vinyloxy)methoxy]adamantane, 2-[(vinyloxy)

methoxy]adamantane, 2-methyl-2-[(vinyloxy)methoxy]adamantane, 1-{[(vinyloxy)methoxy]methyl}adamantane, 1,3-bis-[(vinyloxy)methoxy]adamantane, 1,3-bis{[(vinyloxy)methoxy]methyl}adamantane, 1,3-bis[(vinyloxy)methoxy]perfluoroadamantane, 3-fluoro-1-bis-[(vinyloxy)methoxy]adamantane, 3,5-difluoro-1-[(vinyloxy)methoxy]adamantane, 3,5,7-trifluoro-1-[(vinyloxy)methoxy]adamantane, 1-[(vinyloxy)methoxy]perfluoroadamantane, 4-fluoro-2-methyl-2-[(vinyloxy)-methoxy]adamantane, 5-fluoro-2-methyl-2-[(vinyloxy)-methoxy]adamantane, 2-methyl-2-[(vinyloxy)methoxy]perfluoroadamantane, 1-{[(vinyloxy)methoxy]methyl}perfluoroadamantane, 3-methyl-1-[(vinyloxy)methoxy]adamantane, 3,5-dimethyl-1-[(vinyloxy)methoxy]adamantane, 5,7-dimethyl-2-methyl-2-[(vinyloxy)-methoxy]adamantane, 4-oxo-1-[(vinyloxy)methoxy]-adamantane and 4-oxo-2-[(vinyloxy)methoxy]adamantane.

However, 1-vinyloxyadamantane, 1-vinyloxy-3-hydroxyadamantane, 1-vinyloxy-3,5-dihydroxyadamantane, 1-vinyloxymethyladamantane, 1-vinyloxyethyladamantane, 1,3-divinyloxyadamantane, 1,3-divinyloxy-5-hydroxyadamantane, 1,3,5-trivinyloxyadamantane are excluded from the adamantyl vinyl ether compound of the present invention.

A production process for the adamantyl vinyl ether compound of the present invention represented by Formula (I) may any ones as long as it is a process in which a compound having the structure represented by Formula (I) is obtained, and it may not specifically be restricted. The intended compound can efficiently be produced according to two processes shown below.

In the first process of the present invention, the adamantyl vinyl ether compound represented by Formula (I) described above is produced by subjecting alcohol having an eliminating group in a β position to (a) chloroalkyl-etherification by reacting with hydrogen chloride, then subjecting it to (b) etherification by reacting with an adamantyl group-containing alcohol and a base to form an adamantyl group-containing ether and then subjecting it to (c) vinyl-etherification by reacting with a base.

The reaction steps in the first process of the present invention shall be explained below in order.

(a) Chloroalkyl-etherification

The chloroalkyl-etherification is carried out by melting alcohol having an eliminating group in a β position, aldehyde and ketone or dissolving them in a solvent, then adding a desiccant thereto and blowing dried hydrogen chloride gas thereinto.

In the process of the present invention, the alcohol having an eliminating group in a β position used as the starting material includes, for example, alcohols having an eliminating group such as halogen, p-toluenesulfonate (hereinafter referred to as TosO) and methanesulfonate (hereinafter referred to as MesO) in a β position. To be more specific, 2-chloroethanol, 2-bromoethanol, 2-iodoethanol and 2-hydroxyethyl p-toluenesulfonate can be given.

Acetaldehyde, paraformaldehyde, acetaldehyde, acetone and hexafluoroacetone can be given as the aldehyde and the ketone.

A reaction temperature in carrying out the chloroalkyl-etherification is −200 to 200° C., preferably −78 to 50° C. If the reaction temperature is too low, the reaction speed is reduced to extend the reaction time. On the other hand, if the reaction temperature is too high, side reactions are increased, and hydrogen chloride gas is decreased in a solubility in a solvent, so that a large amount of hydrogen chloride gas is required.

The reaction pressure is 0.01 to 10 MPa, preferably atmospheric pressure to 1 MPa in terms of absolute pressure. If the reaction pressure is too low, hydrogen chloride gas is decreased in a solubility in a solvent, and the reaction time is extended. On the other hand, if the reaction pressure is too high, a specific apparatus is required, and it is disadvantageous in terms of practical use.

The reaction time is one minute to 24 hours, preferably 30 minutes to 5 hours.

A solvent is not necessarily required, but it is preferably used. Advantageously used is a solvent in which a solubility of the alcohol having an eliminating group such as halogen, TosO and MesO in a β position is 0.5% or more, preferably 5% or more. When using the solvent, an amount thereof is controlled to such an amount that a concentration of the above alcohol having an eliminating group in the reaction mixture is 0.5% or more, preferably 5% or more. In this case, the alcohol having an eliminating group in a β position may stay in a suspension state but is preferably dissolved. Moisture contained in the solvent is preferably removed with a desiccant before use. The solvent which can be used includes, to be specific, hydrocarbon base solvents such as hexane and heptane, ether base solvents such as diethyl ether and THF and halogen base solvents such as dichloromethane and carbon tetrachloride. These solvents may be used alone or in combination of two or more kinds thereof.

The desiccant shall not specifically be restricted, and ordinary desiccants can be used. To be specific, it includes anhydrous inorganic salts such as anhydrous magnesium sulfate, anhydrous magnesium chloride, anhydrous iron chloride and anhydrous aluminum chloride, calcium chloride, molecular sieves, diphosphorus pentaoxide, sodium perchlorate, activated alumina, silica gel, calcium hydride and lithium aluminum hydride. These desiccants may be used alone or in combination of two or more kinds thereof. A use amount of the desiccant is suitably selected according to an amount of a moisture content present in the reaction system and the kind of the desiccant.

Dried hydrogen chloride gas is preferably used. A feeding method of hydrogen chloride gas includes a method for feeding it from a commercial bomb and a method for reacting sodium chloride with concentrated sulfuric acid to feed generated hydrogen chloride gas. A feed amount of hydrogen chloride gas shall not specifically be restricted and is selected in a range of usually 1 to 10 times mole, preferably 2 to 3 times mole based on paraformaldehyde used.

The reaction product obtained by the chloroalkyl-etherification can be refined by distillation, crystallization and column separation, and the refining method can suitably be selected according to the properties of the above reaction product and the kind of the impurities.

(b) Etherification

The etherification can be carried out by reacting the reaction product obtained by (a) the chloroalkyl-etherification described above with an adamantyl group-containing alcohol and a base. An adamantyl group-containing ether is formed by this etherification.

The adamantyl group-containing alcohol which can be used includes, for example, 1-adamantanol, 1,3-adamantanediol, 1,3,5-adamantanetriol, 2-adamantanol, 2-methyl-2-adamantanol, 2-ethyl-2-adamantanol, 1-adamantylmethanol, 2-adamantylmethanol, 2-methyl-2-adamantylmethanol, 5-hydroxy-2-adamantanone, 1-perfluoroadamantanol, 1,3- perfluoadamantanediol, 2-hydro-2-perfluoroadamantanol, 2-methyl-2-perfluoroadamantanol, 2-ethyl-2-perfluoroadamantanol, 1-perfluoroadamantylmethanol, 2-hydro-2-perfluoroadamantylmethanol, 2-methyl-2-perfluoroadamantylmethanol, 4-oxo-1-adamantanol and 4-oxo-2-adamantanol.

In the present invention, these adamantyl group-containing alcohols may be used alone or in combination of two or more kinds thereof.

The base shall not specifically be restricted. To be specific, it includes sodium amide, triethylamine, pyridine, N,N-dimethylaniline, 1,5-diazabicyclo[4,3,0]nonene-5 (DBN), 1,8-diazabicyclo[5,4,0]undecene-7 (DBU), sodium hydroxide, potassium hydroxide, sodium hydride, potassium carbonate, silver oxide, sodium methoxide and potassium t-butoxide. These bases may be used alone or in combination of two or more kinds thereof.

A reaction temperature in carrying out the etherification is −200 to 200° C., preferably 0 to 100° C. If the reaction temperature is too low, the reaction speed is reduced to extend the reaction time. On the other hand, if the reaction temperature is too high, side reactions are likely to be increased.

The reaction pressure is 0.01 to 10 MPa, preferably atmospheric pressure to 1 MPa in terms of absolute pressure. If the reaction pressure is too low, the reaction time is extended. On the other hand, if the reaction pressure is too high, a specific apparatus is required, and it is disadvantageous in terms of practical use.

The reaction time is one minute to 24 hours, preferably 4 to 12 hours.

A solvent is not necessarily required, but it is preferably used. Advantageously used is a solvent in which a solubility of the adamantyl group-containing alcohol is 0.5% or more, preferably 5% or more. When using the solvent, an amount thereof is controlled to such an amount that a concentration of the adamantyl group-containing alcohol in the reaction mixture is 0.5% or more, preferably 5% or more. In this case, the adamantyl group-containing alcohol may stay in a suspension state but is preferably dissolved. Moisture contained in the solvent is preferably removed with a desiccant before use. The same solvents as used in (a) the chloroalkyl-etherification described above can be used as the solvent which can be used. These solvents may be used alone or in combination of two or more kinds thereof. Also, the desiccant which can be used includes the same desiccants as used in (a) the chloroalkyl-etherification described above. These desiccants may be used alone or in combination of two or more kinds thereof.

The reaction product obtained by the etherification can suitably be refined in the same manner as in (a) the chloroalkyl-etherification described above.

(c) Vinyl-etherification

The vinyl-etherification can be carried out by reacting the adamantyl group-containing ether which is the reaction product obtained by (b) the etherification described above with a base. The adamantyl vinyl ether compound represented by Formula (I) described above can be obtained by this vinyl-etherification.

The base which can be used shall not specifically be restricted. To be specific, the same bases as used in (b) the etherification described above can be used. These solvents may be used alone or in combination of two or more kinds thereof.

A reaction temperature in carrying out the vinyl-etherification is −200 to 200° C., preferably 0 to 100° C. If the reaction temperature is too low, the reaction speed is reduced to extend the reaction time. On the other hand, if the reaction temperature is too high, side reactions are likely to be increased.

The reaction pressure is 0.01 to 10 MPa, preferably atmospheric pressure to 1 MPa in terms of absolute pressure. If the reaction pressure is too low, the reaction time is extended. On the other hand, if the reaction pressure is too high, a specific apparatus is required, and it is disadvantageous in terms of practical use.

The reaction time is one minute to 24 hours, preferably 1 to 6 hours.

A solvent is not necessarily required, but it is preferably used. Advantageously used is a solvent in which a solubility of the adamantyl group-containing ether is 0.5% or more, preferably 5% or more. When using the solvent, an amount thereof is controlled to such an amount that a concentration of the adamantyl group-containing ether in the reaction mixture is 0.5% or more, preferably 5% or more. In this case, the adamantyl group-containing ether may stay in a suspension state but is preferably dissolved. Moisture contained in the solvent is preferably removed with a desiccant before use. The solvent which can be used includes the same solvents as used in (a) the chloroalkyl-etherification described above. These solvents may be used alone or in combination of two or more kinds thereof. Also, the same desiccants as used in (a) the chloroalkyl-etherification described above can be used as the desiccant. These desiccants may be used alone or in combination of two or more kinds thereof.

The adamantyl vinyl ether compound represented by Formula (I) described above which is obtained by the vinyl-etherification can suitably be refined in the same manner as in (a) the chloroalkyl-etherification described above.

In the second process of the present invention, the adamantane derivative represented by Formula (I) described above is produced by subjecting an adamantyl group-containing alcohol to (a) chloroalkyl-etherification by reacting with hydrogen chloride, then subjecting it to (b) etherification by reacting with alcohol having an eliminating group in a β position and a base to form an adamantyl group-containing ether and then subjecting it to (c) vinyl-etherification by reacting with a base.

The reaction steps in the second process of the present invention shall be explained below in order.

(a) Chloroalkyl-etherification

The chloroalkyl-etherification is carried out by melting an adamantyl group-containing alcohol, aldehyde and ketone or dissolving them in a solvent, then adding a desiccant thereto and blowing dried hydrogen chloride gas thereinto.

The adamantyl group-containing alcohol which can be used includes the same alcohols as used in the first process described above. These adamantyl group-containing alcohols may be used alone or in combination of two or more kinds thereof.

Acetaldehyde, paraformaldehydeacetaldehyde, acetone and hexafluoroacetone can be given as the aldehyde and the ketone.

The same conditions as in (a) the chloroalkyl-etherification in the first process described above can be adopted for a reaction temperature, a reaction pressure and a reaction time in carrying out the chloroalkyl-etherification.

A solvent is not necessarily required, but it is preferably used. Advantageously used is a solvent in which a solubility of the adamantyl group-containing alcohol is 0.5% or more, preferably 5% or more. When using the solvent, an amount thereof is controlled to such an amount that a concentration of the adamantyl group-containing alcohol in the reaction mixture is 0.5% or more, preferably 5% or more. In this case, the adamantyl group-containing alcohol may stay in a suspension state but is preferably dissolved. Moisture contained in the solvent is preferably removed with a desiccant before use. The solvent which can be used includes the same solvents as used in the first process described above. These solvents may be use alone or in combination of two or more kinds thereof. Also, the desiccant which can be used includes the same desiccants as used in the first process described above. These desiccants may be used alone or in combination of two or more kinds thereof.

The same hydrogen chloride gas as used in the first process described above can be used.

The reaction product obtained by the chloroalkyl-etherification can suitably be refined in the same manner as in the first process described above.

(b) Etherification

The etherification can be carried out by reacting the reaction product obtained by (a) the chloroalkyl-etherification described above with alcohol having an eliminating group in a β position and a base. An adamantyl group-containing ether is formed by this etherification.

The same ones as used in the first process described above can be used as the alcohol having an eliminating group in a β position and the base.

The same conditions as in (b) the etherification in the first process described above can be adopted for a reaction temperature, a reaction pressure and a reaction time in carrying out the etherification.

A solvent is not necessarily required, but it is preferably used. Advantageously used is a solvent in which a solubility of the adamantyl group-containing ether is 0.5% or more, preferably 5% or more. When using the solvent, an amount thereof is controlled to such an amount that a concentration of the adamantyl group-containing ether in the reaction mixture is 0.5% or more, preferably 5% or more. In this case, the adamantyl group-containing ether may stay in a suspension state but is preferably dissolved. Moisture contained in the solvent is preferably removed with a desiccant before use. The solvent which can be used includes the same solvents as used in the first process described above. These solvents may be used alone or in combination of two or more kinds thereof. Also, the desiccant which can be used includes the same desiccants as used in the first process described above. These desiccants may be used alone or in combination of two or more kinds thereof.

The reaction product obtained by the etherification can suitably be refined in the same manner as in the first process described above.

(c) Vinyl-etherification

The vinyl-etherification can be carried out by further reacting the reaction product obtained by (b) the etherification described above with a base.

The same ones as used in the first process described above can be used as the base.

The same conditions as in (c) the vinyl-etherification in the first process described above can be adopted for a reaction temperature, a reaction pressure and a reaction time in carrying out the etherification.

A solvent is not necessarily required, but it is preferably used. Advantageously used is a solvent in which a solubility of the adamantyl group-containing ether is 0.5% or more, preferably 5% or more. When using the solvent, an amount thereof is controlled to such an amount that a concentration of the adamantyl group-containing ether in the reaction mixture is 0.5% or more, preferably 5% or more. In this case, the adamantyl group-containing ether may stay in a suspension state but is preferably dissolved. Moisture contained in the solvent is preferably removed with a desiccant before use. The solvent which can be used includes the same solvents as used in the first process described above. These solvents may be used alone or in combination of two or more kinds thereof. Also, the desiccant which can be used includes the same desiccants as used in the first process described above. These desiccants may be used alone or in combination of two or more kinds thereof.

The adamantyl vinyl ether compound represented by Formula (I) described above which is obtained by the vinyl-etherification can suitably be refined in the same manner as in the first process described above.

The adamantyl vinyl ether compound of the second present invention is a novel compound which is not described in documents, and it is the adamantyl vinyl ether compound represented by Formula (II):

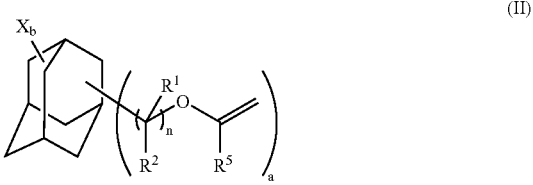

(II)

In Formula (II) described above, the alkyl group having 1 to 10 carbon atoms represented by X, $R^1$ and $R^2$ includes, to be specific, methyl, ethyl, n-propyl, i-propyl, n-butyl, i-butyl, sec-butyl, tert-butyl, n-amyl, i-amyl, n-hexyl, i-hexyl, n-heptyl, i-heptyl, n-octyl, i-octyl, 2-ethyl-hexyl, n-nonyl, i-nonyl, n-decyl and i-decyl.

The halogen atom represented by X, $R^1$ and $R^2$ includes, to be specific, a fluorine atom, a chlorine atom, a bromine atom and an iodine atom.

The alkoxy group having 1 to 8 carbon atoms represented by X includes, to be specific, methoxy, ethoxy, n-propoxy, i-propoxy, n-butoxy, i-butoxybutyl, sec-butoxy, tert-butoxy, n-pentoxy, i-pentoxy, n-hexoxy, i-hexoxy, n-heptoxy, i-heptoxy, n-ocotoxy, i-ocotoxy and 2-ethyl-hexoxy.

COOR (R represents an alkyl group having 1 to 8 carbon atoms) represented by X includes, to be specific, $COOCH_3$, $COOC_2H_5$, $COO\text{-n-}C_3H_7$, $COO\text{-i-}C_3H_7$, $COO\text{-n-}C_4H_9$, $COO\text{-i-}C_4H_9$, $COO\text{-sec-}C_4H_9$, $COO\text{-tert-}C_4H_9$, $COO\text{-n-}C_5H_{11}$, $COO\text{-i-}C_5H_{11}$, $COO\text{-n-}C_6H_{13}$, $COO\text{-i-}C_6H_{13}$, $COO\text{-n-}C_7H_{15}$, $COO\text{-i-}C_7H_{15}$, $COO\text{-n-}C_8H_{17}$ and $COO\text{-i-}C_8H_{17}$.

X represents a hydrogen atom, a halogen atom, an alkyl group having 1 to 10 carbon atoms which may contain a hetero element, a hydroxyl group, an alkoxy group having 1 to 8 carbon atoms, a carboxyl group, COOR (R represents an alkyl group having 1 to 8 carbon atoms) or =O (keto group) formed by putting two X's together. They are independent from each other, and all of them may be the same or different.

$R^1$ and $R^3$ represents a hydrogen atom, a halogen atom or an alkyl group having 1 to 10 carbon atoms which may contain a hetero element, and $R^5$ represents a hydrogen atom, a halogen atom or an alkyl group having 1 to 3 carbon atoms which may contain a hetero element. They are independent from each other, and all of them may be the same or different.

The alkyl groups in the alkyl group having 1 to 10 carbon atoms, the alkoxy group having 1 to 8 carbon atoms and the alkoxycarbonyl group in which an alkyl group has 1 to 8 carbon atoms were explained above. They are independent from each other, and all of them may be the same or different.

In Formula (II), n's each represent an integer of 0 to 10; a represents an integer of 1 to 4; b represents an integer of 12 to 15, and a+b is 16. When they are plural, they may be the same as or different from each other. In Formula (II), however, excluded from the adamantyl vinyl ether compound of the present invention are a structure in which only 1 to 3 vinyloxy groups are bonded to a bridge head position of the adamantyl group, a structure in which only one vinyloxymethyl group, vinyloxyethyl group or vinyloxypropyl group is bonded to a bridge head position of the adamantyl group and a structure in which only a vinyloxy group and a hydroxyl group are bonded to a bridge head position of the adamantyl group.

Among them, the compound having a vinyloxy group is preferred.

The specific examples of the adamantyl vinyl ether compound of the present invention represented by Formula (II) include 3-fluoro-1-(vinyloxy)adamantane, 3,5-difluoro-1-(vinyloxy)adamantane, 3,5,7-trifluoro-1-(vinyloxy)adamantane, 1-(vinyloxy)perfluoroadamantane, 2-(vinyloxy)adamantane, 4-fluoro-2-methyl-2-(vinyloxy)adamantane, 5-fluoro-2-methyl-2-(vinyloxy)adamantane, 2-methyl-2-(vinyloxy)-perfluoroadamantane, 3-fluoro-1-[(vinyloxy)-methyl]adamantane, 1-[(vinyloxy)methyl]perfluoroadamantane, 3-methyl-1-(vinyloxy)adamantane, 3,5-dimethyl-1-(vinyloxy)adamantane, 5,7-dimethyl-2-methyl-2-(vinyloxy)adamantane, 5-fluoro-1,3-bis(vinyloxy)adamantane, 5,7-difluoro-1,3-bis(vinyloxy)adamantane, 5-methyl-1,3-bis(vinyloxy)adamantane, 5,7-dimethyl-1,3-bis(vinyloxy)adamantane and 4-oxo-2-(vinyloxy)adamantane.

The production process for the adamantyl vinyl ether compound of the present invention represented by Formula (II) may be any ones as long as it is a process in which the compound having the structure represented by Formula (II) described above is obtained, and it shall not specifically be restricted. However, the intended compound can efficiently be produced according to the following two processes of the present invention.

In the second process-1 of the present invention, the adamantyl vinyl ether compound represented by Formula (II) is produced by reacting an adamantyl group-containing alcohol with an olefin represented by Formula (III) and a base:

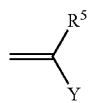

(III)

In Formula (III) described above, the eliminating group represented by Y includes, to be specific, halogen, TosO and MesO. $R^5$ represents a hydrogen atom, a halogen atom or an alkyl group having 1 to 3 carbon atoms which may contain a hetero element. They are independent from each other, and all of them may be the same or different.

The olefin represented by Formula (III) includes, to be specific, vinyl chloride and vinyl bromide.

The adamantyl group-containing alcohol which can be used includes, for example, 2-ethyl-2-adamantanol, 2-adamantylmethanol, 2-methyl-2-adamantylmethanol, 1-perfluoroadamantanol, 1,3-perfluoroadamantanediol, 2-hydro-2-perfluoroadamantanol, 2-methyl-2-perfluoroadamantanol, 2-ethyl-2-perfluoroadamantanol, 1-perfluoroadamantylmethanol, 2-hydro-2-perfluoroadamantylmethanol, 2-methyl-2-perfluoroadamantylmethanol, 4-oxo-1-adamantanol and 4-oxo-2-adamantanol. These adamantyl group-containing alcohols may be used alone or in combination of two or more kinds thereof.

The base which can be used includes the same bases as used in the first process described above. These bases may be used alone or in combination of two or more kinds thereof.

The reaction temperature is −78 to 200° C., preferably 0 to 100° C. If the reaction temperature is too low, the reaction speed is reduced to extend the reaction time. On the other hand, if the reaction temperature is too high, side reactions are likely to be increased.

The reaction pressure is 0.01 to 10 MPa, preferably atmospheric pressure to 2 MPa in terms of absolute pressure. If the reaction pressure is too low, the reaction time is extended. On the other hand, if the reaction pressure is too high, a specific apparatus is required, and it is disadvantageous in terms of practical use.

The reaction time is one minute to 24 hours, preferably 30 minutes to 5 hours.

A solvent is not necessarily required, but it is preferably used. Advantageously used is a solvent in which a solubility of the adamantyl group-containing alcohol is 0.5% or more, preferably 5% or more. When using the solvent, an amount thereof is controlled to such an amount that a concentration of the adamantyl group-containing alcohol in the reaction mixture is 0.5% or more, preferably 5% or more. In this case, the adamantyl group-containing alcohol may stay in a suspension state but is preferably dissolved. Moisture contained in the solvent is preferably removed with a desiccant before use. The solvent which can be used includes the same solvents as used in the first process described above. These solvents may be used alone or in combination of two or more kinds thereof. Also, the desiccant which can be used includes the same desiccants as used in first process described above. These desiccants may be used alone or in combination of two or more kinds thereof.

The reaction product thus obtained can be refined by distillation, crystallization and column separation, and a refining method can suitably be selected according to the properties of the above reaction product and the kind of the impurities.

In the second process-2 of the present invention, the adamantyl vinyl ether compound represented by Formula (II) is produced by reacting an adamantyl group-containing alcohol with an acetylene derivative represented by Formula (IV) and a base:

(IV)

In Formula (IV) described above, $R^5$ represents a hydrogen atom, a halogen atom or an alkyl group having 1 to 3 carbon atoms which may contain a hetero element. They are independent from each other, and all of them may be the same or different.

The acetylene derivative represented by Formula (IV) includes, to be specific, acetylene, methylacetylene and ethylacetylene.

The adamantyl group-containing alcohol which can be used includes the same ones as used in the second process-1 described above. These adamantyl group-containing alcohols may be used alone or in combination of two or more kinds thereof.

The base which can be used includes the same bases as used in the first process described above. These bases may be used alone or in combination of two or more kinds thereof.

The same conditions as in the second process-1 described above can be adopted for the reaction temperature, the reaction pressure and the reaction time.

The solvent and the desiccant which can be used include the same ones as used in the second process-1 described above.

The reaction product thus obtained can suitably be refined in the same manner as in the second process-1 described above.

The adamantyl vinyl ether compound of the present invention thus obtained is a novel compound, and it is useful as a monomer for functional resins (a photosensitive resin and the like) in the photolithography field or a raw material therefor, a resin additive (a heat resistance-improving agent and the like), other various additives (an acidity-raising agent, a fat solubility-raising agent and the like), medical and agricultural intermediates and other various industrial products.

The polymer of the above compound has both of a high dry etching resistance in adamantane and an excellent transparency even at a short wavelength, and it can be used particularly as a resist resin for an $F_2$ eximer laser.

Further, the adamantyl vinyl ether compound of the present invention can be expected to be used as an optical material including optical fibers, optical waveguides and optical disc substrates.

EXAMPLES

Next, the present invention shall be explained in further details with reference to examples, but the present invention shall by no means be restricted by these examples.

Example 1

(1) Synthesis of 2-chloroethyl chloromethyl ether

A Kjeldahl flask of 50 ml equipped with a nozzle for introducing hydrogen chloride gas into which a stirrer was put was charged with 0.81 g (10 mmol) of 2-chloroethanol, 0.30 g (10 mmol) of paraformaldehyde, 0.60 g (50 mmol) of magnesium sulfate and dried dichloromethane, and it was stirred at a room temperature. Hydrogen chloride gas which was generated by mixing 10 g of sodium chloride with 50 ml of concentrated sulfuric acid was blown thereinto through the nozzle for 2 hours. After stirred for further 2 hours, magnesium sulfate was filtered, and then gas chromatographic analysis was carried out to find that 2-chloroethanol was converted by 95% and that 1.03 g (8.0 mmol, isolation yield: 80.6%) of a colorless liquid of chloroethyl chloromethyl ether was obtained at a selectivity of 89.5%.

The results of gas chromatography mass analysis (GC-MS, EI method) are shown below:

m/e: 128 (M, 0.07%), 93 (55.9%), 63 (30.0%), 49 (35.6%), 79 (100%)

(2) Synthesis of 1-[(2-chloroethoxy)methoxy]adamantane

A two neck Kjeldahl flask of 50 ml into which a stirrer was put was charged with 1.55 g (12 mmol) of chloroethyl chloromethyl ether obtained in (1), 1.52 g (10 mmol) of 1-adamantanol, 1.52 g (15 mmol) of triethylamine and dried THF, and it was equipped with a coiled condenser to reflux and stir the solution for 8 hours. Triethylamine hydrochloride was filtered, and gas chromatographic analysis was carried out to find that 1-adamantanol was converted by 68.2% and that 2.04 g (8.3 mmol, isolation yield: 83.3%) of a colorless liquid which was the intended product was obtained at a selectivity of 96.5%.

The results of gas chromatography mass analysis (GC-MS, EI method) are shown below:

m/e: 244 (M, 13.3%), 107 (75.3%), 93 (61.6%), 63 (37.2%), 135 (100%)

(3) Synthesis of 1-[(vinyloxy)methoxy]adamantane

A two neck Kjeldahl flask of 50 ml into which a stirrer was put was charged with 2.45 g (10 mmol) of 1-[(2-chloroethoxy)methoxy]adamantane obtained in (2), 1.68 g (15 mmol) of potassium t-butoxide and dried THF, and it was equipped with a coiled condenser to reflux and stir the solution for 2 hours. Potassium hydrochloride was filtered, and gas chromatographic analysis was carried out to find that the compound obtained in (2) was completely converted and that 1.79 g (8.6 mmol, isolation yield: 85.9%) of a colorless liquid (the intended product) represented by the following formula was obtained at a selectivity of 99.5%:

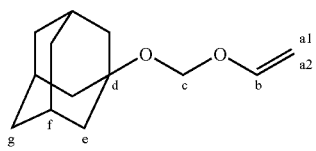

The results of gas chromatography mass analysis (GC-MS, EI method) and spectral analysis ($^1$H-NMR, $^{13}$C-NMR) are shown below:

m/e: 208 (M, 0.08%), 93 (21.0%), 79 (20.5%), 67 (7.3%), 135 (100%). $^1$H-NMR: 1.63 (e or g), 1.81 (e or g), 2.14 (f), 4.07 (a2), 4.38 (a1), 5.01 (c), 6.41 (b). $^{13}$C-NMR: 30.5 (f), 36.1 (e or g), 42.3 (e or g), 74.3 (d), 87.6 (c), 89.9 (a), 149.6 (b)

Example 2

(1) Synthesis of 2-methyl-2-[(2-chloroethoxy)methoxy]adamantane

A two neck Kjeldahl flask of 50 ml into which a stirrer was put was charged with 1.55 g (12 mmol) of chloroethyl chloromethyl ether obtained in Example 1 (1), 1.66 g (10 mmol) of 2-methyl-2-adamantanol, 1.52 g (15 mmol) of triethylamine and dried THF, and it was equipped with a coiled condenser to reflux and stir the solution for 8 hours. Triethylamine hydrochloride was filtered, and gas chromatographic analysis was carried out to find that 2-methyl-2-adamantanol was converted by 46.2% and that 2.04 g (7.9 mmol, isolation yield: 78.8%) of a colorless liquid which was the intended product was obtained at a selectivity of 97.3%.

The results of gas chromatography mass analysis (GC-MS, EI method) are shown below:

m/e: 243 (M, 34.6%), 149 (71.0%), 148 (76.5%), 79 (33.5%), 93 (100%)

(2) Synthesis of 2-methyl-2-[(vinyloxy)methoxy]adamantane

A two neck Kjeldahl flask of 50 ml into which a stirrer was put was charged with 2.59 g (10 mmol) of 2-methyl-2-[(2-chloroethoxy)methoxy]adamantane obtained in (1), 1.68 g (15 mmol) of potassium t-butoxide and dried THF, and it was equipped with a coiled condenser to reflux and stir the solution for 2 hours. Potassium hydrochloride was filtered, and gas chromatographic analysis was carried out to find that the compound obtained in (1) was completely converted and that 1.89 g (8.5 mmol, isolation yield: 85.0%) of a colorless liquid which was the intended product was obtained at a selectivity of 99.5%.

The results of gas chromatography mass analysis (GC-MS, EI method) are shown below:

m/e: 207 (M—CH₃, 0.16%), 93 (19.7%), 150 (13.7%), 81 (13.1%), 149 (100%)

Example 3

(1) Synthesis of 1-adamantylmethyl chloromethyl ether

A Kjeldahl flask of 50 ml equipped with a nozzle for introducing hydrogen chloride gas into which a stirrer was put was charged with 1.66 g (10 mmol) of 1-adamantylmethanol, 0.60 g (20 mmol) of paraformaldehyde, 1.20 g (10 mmol) of magnesium sulfate and dried dichloromethane, and it was cooled down to 0° C. and stirred in an ice bath. Hydrogen chloride gas which was generated by mixing 10 g of sodium chloride with 50 ml of conc. sulfuric acid was blown thereinto through the nozzle for 60 minutes. After stirred for further 60 minutes, magnesium sulfate was filtered, and then gas chromatographic analysis was carried out to find that 1-adamantylmethanol was completely converted and that 1.67 g (7.8 mmol, isolation yield: 77.8%) of a colorless liquid which was the intended product was obtained at a selectivity of 94.5%.

The results of gas chromatography mass analysis (GC-MS, EI method) are shown below:

m/e: 214 (M, 0.5%), 178 (11.0%), 149 (5.8%), 135 (100%)

(2) Synthesis of 1-{[(2-chloroethoxy)methoxy]methyl}adamantane

A two neck Kjeldahl flask of 50 ml into which a stirrer was put was charged with 2.15 g (10 mmol) of 1-adamantylmethyl chloromethyl ether obtained in (1), 0.97 g (12 mmol) of 2-chloroethanol, 1.52 g (15 mmol) of triethylamine and dried THF, and it was equipped with a coiled condenser to reflux and stir the solution for 8 hours. Triethylamine hydrochloride was filtered, and gas chromatographic analysis was carried out to find that chloroethyl chloromethyl ether was completely converted and that 2.25 g (8.7 mmol, isolation yield: 86.9%) of a colorless liquid which was the intended product was obtained at a selectivity of 98.5%.

The results of gas chromatography mass analysis (GC-MS, EI method) are shown below:

m/e: 209 (0.03%), 178 (22.4%), 93 (20.1%), 149 (16.7%), 135 (100%)

(3) Synthesis of 1-{[(vinyloxy)methoxy]methyl}adamantane

A two neck Kjeldahl flask of 50 ml into which a stirrer was put was charged with 2.59 g (10 mmol) of 1-{[(2-chloroethoxy)methoxy]methyl}adamantane obtained in (2), 1.68 g (15 mmol) of potassium t-butoxide and dried THF, and it was equipped with a coiled condenser to reflux and stir the solution for 2 hours. Potassium hydrochloride was filtered, and gas chromatographic analysis was carried out to find that the compound obtained in (2) was completely converted and that 1.96 g (8.8 mmol, isolation yield: 88.1%) of a colorless liquid which was the intended product was obtained at a selectivity of 99.5%.

The results of gas chromatography mass analysis (GC-MS, EI method):

m/e: 179 (5.8%), 107 (14.1%), 93 (25.9%), 81 (14.3%), 149 (100%)

Example 4

(1) Synthesis of 4-oxo-2-[(2-chloroethoxy)methoxy]adamantane

A two neck Kjeldahl flask of 50 ml into which a stirrer was put was charged with 1.55 g (12 mmol) of 2-chloroethyl chloromethyl ether obtained in Example 1 (1), 1.66 g (10 mmol) of 4-oxo-2-adamantanol, 1.52 g (15 mmol) of triethylamine and dried THF, and it was equipped with a coiled condenser to reflux and stir the solution for 8 hours. Triethylamine hydrochloride was filtered, and gas chromatographic analysis was carried out to find that 4-oxo-2-adamantanol was converted by 98.3 and that 2.56 g (9.8 mmol, isolation yield: 97.6%) of a colorless liquid which was the intended product was obtained at a selectivity of 99.3%.

The results of gas chromatography mass analysis (GC-MS, EI method) are shown below:

m/e: 258 (M, 1.3%), 260 (M+2, 0.5%), 149 (45.8%), 95 (35.2%), 93 (100.0%), 63 (67.7%)

(2) Synthesis of 4-oxo-2-[(vinyloxy)methoxy]adamantane

A two neck Kjeldahl flask of 50 ml into which a stirrer was put was charged with 2.45 g (10 mmol) of 4-oxo-2-[(2-chloroethoxy)methoxy]adamantane obtained in (1), 1.68 g (15 mmol) of potassium t-butoxide and dried THF, and it was equipped with a coiled condenser to reflux and stir the solution for 2 hours. Potassium hydrochloride was filtered, and gas chromatographic analysis was carried out to find that 4-oxo-2-[(2-chloroethoxy)methoxy]adamantane was completely converted and that 2.20 g (9.9 mmol, isolation yield: 98.9%) of a colorless liquid (the intended product) represented by the following formula was obtained at a selectivity of 98.9%:

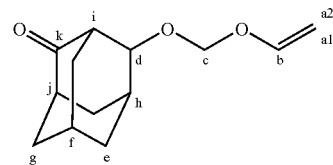

The results of gas chromatography mass analysis (GC-MS, EI method) and spectral analysis (¹H-NMR, ¹³C-NMR) are shown below:

m/e: 222 (M, 0.2%), 179 (18.2%), 121 (100.0%), 93 (42.8%), 79 (59.4%). ¹H-NMR: 1.88 (e or g), 1.96 (e or g), 2.04 (e or g), 2.18 (f or h), 2.33 (f or h), 2.50 (i or j), 2.74 (i or j), 4.14 (a2, d), 4.46 (a1), 4.93 (c), 6.39 (b). ¹³C-NMR: 26.3 (f), 31.9 (h), 33.1 (e or g), 35.1 (e or g), 37.9 (e or g), 38.9 (e or g), 46.3 (j), 51.5 (i), 83.2 (d), 91.3 (c), 91.9 (a), 149.4 (b), 215.7 (k)

Example 5

(1) Synthesis of 2-[(2-chloroethoxy)methoxy]adamantane

A two neck Kjeldahl flask of 50 ml into which a stirrer was put was charged with 1.55 g (12 mmol) of 2-chloroethyl chloromethyl ether obtained in Example 1 (1), 1.52 g (10 mmol) of 2-adamantanol, 1.52 g (15 mmol) of triethylamine and dried THF, and it was equipped with a coiled condenser to reflux and stir the solution for 8 hours. Triethylamine hydrochloride was filtered, and gas chromatographic analysis was carried out to find that 2-adamantanol was converted by 97.6% and that 2.35 g (9.6 mmol, isolation yield: 96.2%) of a colorless liquid which was the intended product was obtained at a selectivity of 98.6%.

The results of gas chromatography mass analysis (GC-MS, EI method) are shown below:

m/e: 244 (M, 0.2%), 214 (5.3%), 165 (8.9%), 134 (100.0%), 92 (33.3%)

(2) Synthesis of 2-[(vinyloxy)methoxy]adamantane

A two neck Kjeldahl flask of 50 ml into which a stirrer was put was charged with 2.45 g (10 mmol) of 2-[(2-chloroethoxy)methoxy]adamantane obtained in (1), 1.68 g (15 mmol) of potassium t-butoxide and dried THF, and it was equipped with a coiled condenser to reflux and stir the solution for 2 hours. Potassium hydrochloride was filtered, and gas chromatographic analysis was carried out to find that 2-[(2-chloroethoxy)methoxy]adamantane was completely converted and that 2.06 g (9.9 mmol, isolation yield: 98.7%) of a colorless liquid (the intended product) represented by the following formula was obtained at a selectivity of 98.7%:

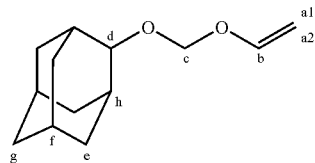

The results of gas chromatography mass analysis (GC-MS, EI method) and spectral analysis ($^1$H-NMR, $^{13}$C-NMR) are shown below:

m/e: 208 (M, 0.1%), 165 (9.0%), 135 (100.0%), 93 (36.3%), 79 (33.2%). $^1$H-NMR: 1.49 (e or g), 1.69 (e or g), 1.81 (e or g), 1.99 (f), 2.05 (h), 3.73 (d), 4.10 (a2), 4.46 (a1), 4.97 (c), 6.44 (b). $^{13}$C-NMR: 27.2 (f, h), 31.4 (e or g), 32.3 (e or g), 36.5 (e or g), 37.6 (e or g), 81.0 (d), 90.3 (c), 92.6 (a), 149.7 (b)

Example 6

(1) Synthesis of 1,3-bis[(2-chloroethoxy)methoxy]perfluoroadamantane

A two neck Kjeldahl flask of 50 ml into which a stirrer was put was charged with 3.65 g (24 mmol) of 2-chloroethyl chloromethyl ether obtained in Example 1 (1), 4.20 g (10 mmol) of 1,3-perfluoroadamantanediol, 3.04 g (30 mmol) of triethylamine and dried THF, and it was equipped with a coiled condenser to reflux and stir the solution for 2 hours. Triethylamine hydrochloride was filtered, and gas chromatographic analysis was carried out to find that 1,3-perfluoroadamantanediol was converted by 78.9% and that 4.60 g (7.6 mmol, isolation yield: 76.3%) of a colorless liquid which was the intended product was obtained at a selectivity of 96.7%.

The results of gas chromatography mass analysis (GC-MS, EI method) are shown below:

m/e: 555 (0.5%), 525 (35.6%), 481 (15.2%), 93 (100.0%), 63 (50.3%)

(2) Synthesis of 1,3-bis[(vinyloxy)methoxy]perfluoroadamantane

A two neck Kjeldahl flask of 50 ml into which a stirrer was put was charged with 5.32 g (10 mmol) of 1,3-bis[(2-chloroethoxy)methoxy]perfluoroadamantane obtained in (1), 3.37 g (30 mmol) of potassium t-butoxide and dried THF, and it was equipped with a coiled condenser to reflux and stir the solution for 2 hours. Potassium hydrochloride was filtered, and gas chromatographic analysis was carried out to find that 1,3-bis[(2-chloroethoxy)methoxy]perfluoroadamantane was completely converted and that 5.11 g (9.6 mmol, isolation yield: 96.2%) of a colorless liquid (the intended product) represented by the following formula was obtained at a selectivity of 96.2%:

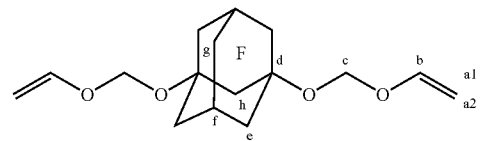

The results of gas chromatography mass analysis (GC-MS, EI method) and spectral analysis ($^1$H-NMR, $^{13}$C-NMR, $^{19}$F-NMR) are shown below:

m/e: 531 (0.2%), 489 (5.2%), 99 (18.7%), 69 (18.6%), 57 (100.0%) $^1$H-NMR: 4.34 (a1), 4.67 (a2), 5.49 (c), 6.42 (b). $^{13}$C-NMR: 92.4 (a), 93.8 (c), 110.0 (d or e or f or g or h), 112.0 (d or e or f or g or h), 112.9 (d or e or f or g or h), 114.1 (d or e or f or g or h), 115.1 (d or e or f or g or h), 116.2 (d or e or f or g or h), 117.1 (d or e or f or g or h), 148.7 (b) $^{19}$F-NMR: −220.7 (f), −121.4 (g or h), −117.4 (e), −113.7 (g or h)

INDUSTRIAL APPLICABILITY

The adamantyl vinyl ether compound of the present invention is useful as a monomer for functional resins (a photosensitive resin and the like) in the photolithography field or a raw material therefor, a resin additive (a heat resistance-improving agent and the like), other various additives (an acidity-raising agent, a fat solubility-raising agent and the like), medical and agricultural intermediates and other various industrial products.

The polymer of the above compound has both of a high dry etching resistance in adamantane and an excellent transparency even at a short wavelength, and it can be used particularly as a resist resin for an $F_2$ eximer laser.

Further, the adamantyl vinyl ether compound of the present invention can be expected to be used as an optical material including optical fibers, optical waveguides and optical disc substrates.

What is claimed is:

1. An adamantyl vinyl ether compound represented by Formula (I):

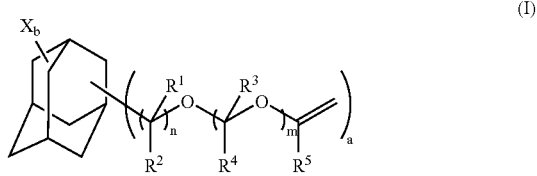

wherein X's each represent independently a hydrogen atom, a halogen atom, an alkyl group having 1 to 10 carbon atoms which may contain a hetero element, a hydroxyl group, an alkoxy group having 1 to 8 carbon atoms, a carboxyl group, COOR (R represents an alkyl group having 1 to 8 carbon atoms) or =O (keto group) formed by putting two X's together; $R^1$, $R^2$, $R^3$ and $R^4$ each represent independently a hydrogen atom, a halogen atom or an alkyl group having 1 to 10 carbon atoms which may contain a hetero element; $R^5$'s each represent independently a hydrogen atom, a halogen atom or an alkyl group having 1 to 3 carbon atoms which may contain a hetero element; m represents an integer of 1 to 10 and n represents an integer of 0; a represents an integer of 1 to 4; b represents an integer of 12 to 15, and a+b is 16; provided that excluded are a structure in which only 1 to 3 vinyloxy groups arc bonded to a bridge head position of the adamantyl group, a structure in which only one vinyloxymethyl group, vinyloxyethyl group or vinyloxypropyl group is bonded to a bridge head position of the adamantyl group and a structure in which only a vinyloxy group and a hydroxyl group are bonded to a bridge head position of the adamantyl group.

2. The adamantyl vinyl ether compound as described in claim 1, having a (vinyloxy)methoxy group.

3. A production process for the adamantyl vinyl ether compound of claim 1, comprising subjecting alcohol having an eliminating group in a β position to (a) chloroalkyl-etherification by reacting with hydrogen chloride, then subjecting it to (b) etherification by reacting with an adamantyl group-containing alcohol and a base to form an adamantyl group-containing ether and then subjecting it to (c) vinyl-etherification by reacting with a base.

4. A production process for the adamantyl vinyl ether compound of claim 1, comprising subjecting an adamantyl group-containing alcohol to (a) chloroalkyl-etherification by reacting with hydrogen chloride, then subjecting it to (b) etherification by reacting with alcohol having an eliminating group in a β position and a base to form an adamantyl group-containing ether and then subjecting it to (c) vinyl-etherification by reacting with a base.

* * * * *

UNITED STATES PATENT AND TRADEMARK OFFICE
CERTIFICATE OF CORRECTION

PATENT NO. : 7,402,712 B2
APPLICATION NO. : 10/862423
DATED : July 22, 2008
INVENTOR(S) : Naoyoshi Hatakeyama et al.

It is certified that error appears in the above-identified patent and that said Letters Patent is hereby corrected as shown below:

On the title page, Item (73), the Assignee information is incorrect. Item (73) should read:

-- (73) Assignee: Idemitsu Kosan Co., Ltd. Tokyo (JP) --

Signed and Sealed this

Eleventh Day of November, 2008

JON W. DUDAS
*Director of the United States Patent and Trademark Office*